US008298286B2

(12) United States Patent
Trieu

(10) Patent No.: US 8,298,286 B2
(45) Date of Patent: Oct. 30, 2012

(54) NON-LINEAR VERTEBRAL MESH

(75) Inventor: Hai H. Trieu, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1289 days.

(21) Appl. No.: 11/612,634

(22) Filed: Dec. 19, 2006

(65) Prior Publication Data

US 2008/0147098 A1    Jun. 19, 2008

(51) Int. Cl.
*A61F 2/44*      (2006.01)

(52) U.S. Cl. ............... 623/17.11; 623/17.13; 623/17.15

(58) Field of Classification Search .................. None
See application file for complete search history.

(56) References Cited

U.S. PATENT DOCUMENTS

| | | | |
|---|---|---|---|
| 4,187,558 A | 2/1980 | Dahlen et al. | |
| 4,467,838 A | 8/1984 | Rheaume | |
| 4,642,119 A | 2/1987 | Shah | |
| 4,832,978 A | 5/1989 | Lesser | |
| 5,061,283 A | 10/1991 | Silvestrini | |
| 5,147,400 A | 9/1992 | Kaplan et al. | |
| 5,571,189 A | 11/1996 | Kuslich | |
| 5,599,585 A | 2/1997 | Cohen | |
| H1643 H | 4/1997 | Hay | |
| 5,711,960 A * | 1/1998 | Shikinami | 424/426 |
| 6,093,205 A | 7/2000 | McLeod et al. | |
| 6,465,073 B1 | 10/2002 | Morman et al. | |
| 6,475,600 B1 | 11/2002 | Morman et al. | |
| 6,585,769 B1 | 7/2003 | Muhanna et al. | |
| 6,737,053 B1 | 5/2004 | Goh et al. | |
| 6,899,945 B2 | 5/2005 | Smalley et al. | |
| 6,946,003 B1 | 9/2005 | Wolowacz et al. | |
| 2002/0123750 A1 * | 9/2002 | Eisermann et al. | 606/69 |

OTHER PUBLICATIONS

Unpublished U.S. Appl. No. 11/413,448, filed Apr. 28, 2006 titled "Vertebral Stabilizer".
Unpublished U.S. Appl. No. 11/400,913, filed Apr. 10, 2006 titled "Elastic Plates for Spinal Fixation or Stabilization".
Unpublished U.S. Appl. No. 11/429,818, filed May 8, 2006 titled "Load Bearing Flexible Spinal Connecting Element".

* cited by examiner

*Primary Examiner* — David Isabella
*Assistant Examiner* — Joshua Levine

(57) ABSTRACT

A vertebral augmentation system comprising a biocompatible mesh sheet having a first end and a second end. The mesh sheet includes a plurality of first strands having a first maximum extension intertwined with a plurality of second strands having a second maximum extension. The mesh sheet also includes a first interface portion adapted to contact a first vertebral bone and a second interface portion adapted to contact a second vertebral bone. The plurality of first strands have a greater elasticity than the plurality of second strands, and the plurality of second strands limit the plurality of first strands from reaching the first maximum extension when the first vertebral bone moves relative to the second vertebral bone.

26 Claims, 5 Drawing Sheets

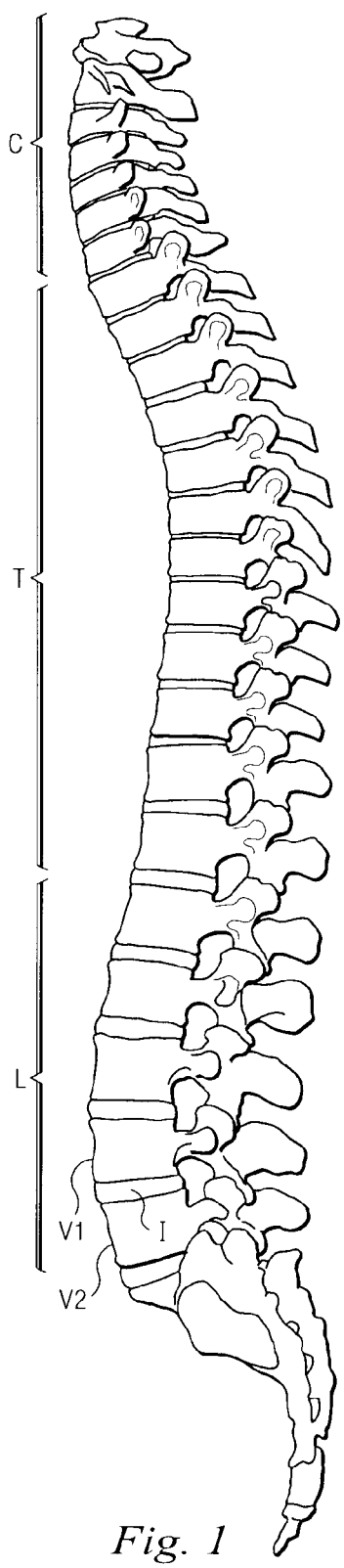
Fig. 1
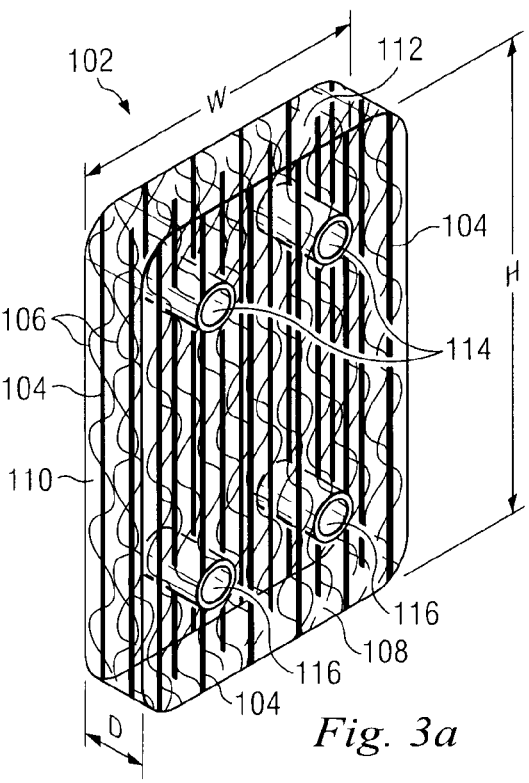
Fig. 3a
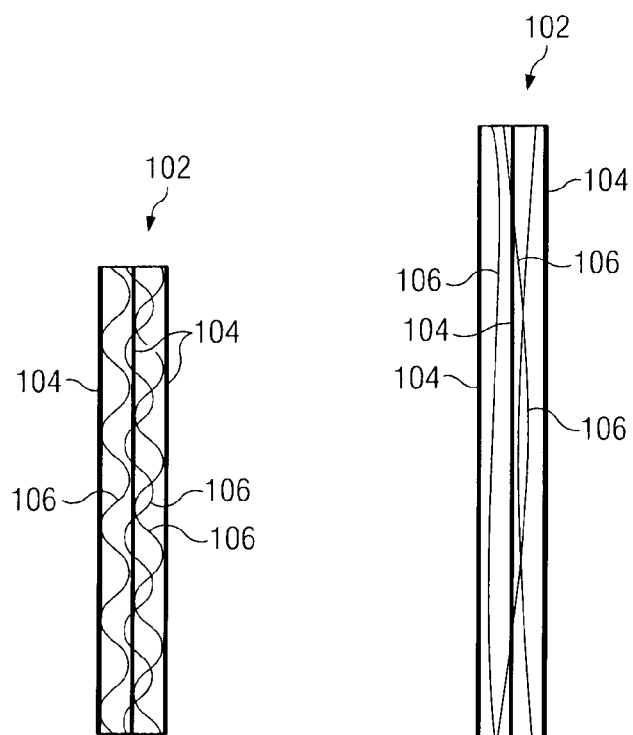
Fig. 3b
Fig. 3c

US 8,298,286 B2

NON-LINEAR VERTEBRAL MESH

BACKGROUND

Severe back pain, limited motion, and nerve damage may be caused by injured, degraded, or diseased spinal joints and particularly, the vertebral discs and ligaments associated with those joints. In a healthy intervertebral joint, the intervertebral disc permits rotation, lateral bending, flexion, and extension motions while the ligaments protect the joint from tension, torsion and shear forces. As the intervertebral joint deteriorates, the intervertebral disc may become compressed, displaced, or herniated, resulting in excess pressure in other areas of the spine. Additionally, the connective ligaments holding the joint together may become impaired. Current methods of treating these damaged discs and ligaments fail to adequately approximate the behavior of native tissues. Therefore, a more naturally functioning solution is desired.

SUMMARY

In one embodiment, a vertebral augmentation system comprising a biocompatible mesh plate having a first end and a second end. The mesh plate includes a plurality of first strands, having a first maximum extension, intertwined with a plurality of second strands having a second maximum extension. The mesh plate also includes a first interface portion adapted to contact a first vertebral bone and a second interface portion adapted to contact a second vertebral bone. The plurality of first strands have a greater elasticity than the plurality of second strands, and the plurality of second strands limit the plurality of first strands from reaching the first maximum extension when the first vertebral bone moves relative to the second vertebral bone.

In another embodiment, a multi-dimensional, bio-compatible mesh of elastic and inelastic strands has a first end adapted to engage an anterior face of a first vertebral bone and a second end adapted to engage an anterior face of a second vertebral bone. The elastic strands extend between the first end and the second end and are adapted to traverse a space between the first and second vertebral bones. The elastic strands having a first elasticity and a first length. The inelastic strands extend between the first end and the second end, and are adapted to traverse the space between the first and second vertebral bones. The inelastic strands have less elasticity than the elastic strands and a second length different from the first length. The inelastic strands are configured to prevent overextension of the elastic strands.

A surgical method comprises the steps of accessing the anterior side of a vertebral disc and the anterior walls of a first vertebral body and a second vertebral body and securing one end of an artificial vertebral mesh system to the first vertebral body with a first bone fixation element. The artificial vertebral mesh system has first strands and second strands adapted to limit extension of the first strands. The surgical method further includes extending the artificial vertebral mesh across the vertebral disc and securing an opposite end of the artificial vertebral mesh system to the second vertebral body with a second bone fixation element. The surgical method further comprises placing the first strands in tension while the second strands remain slack.

Additional embodiments are included in the attached drawings and the description provided below.

BRIEF DESCRIPTION OF THE DRAWINGS

FIG. 1 is a sagittal view of a vertebral column.

FIG. 3a is a perspective view of the vertebral augmentation system of FIG. 2.

FIG. 3b is a cross sectional view of the vertebral augmentation system of FIG. 2 in an unloaded state.

FIG. 3c is a cross sectional view of the vertebral augmentation system of FIG. 2 under tensile loading.

DETAILED DESCRIPTION

Figure 2:
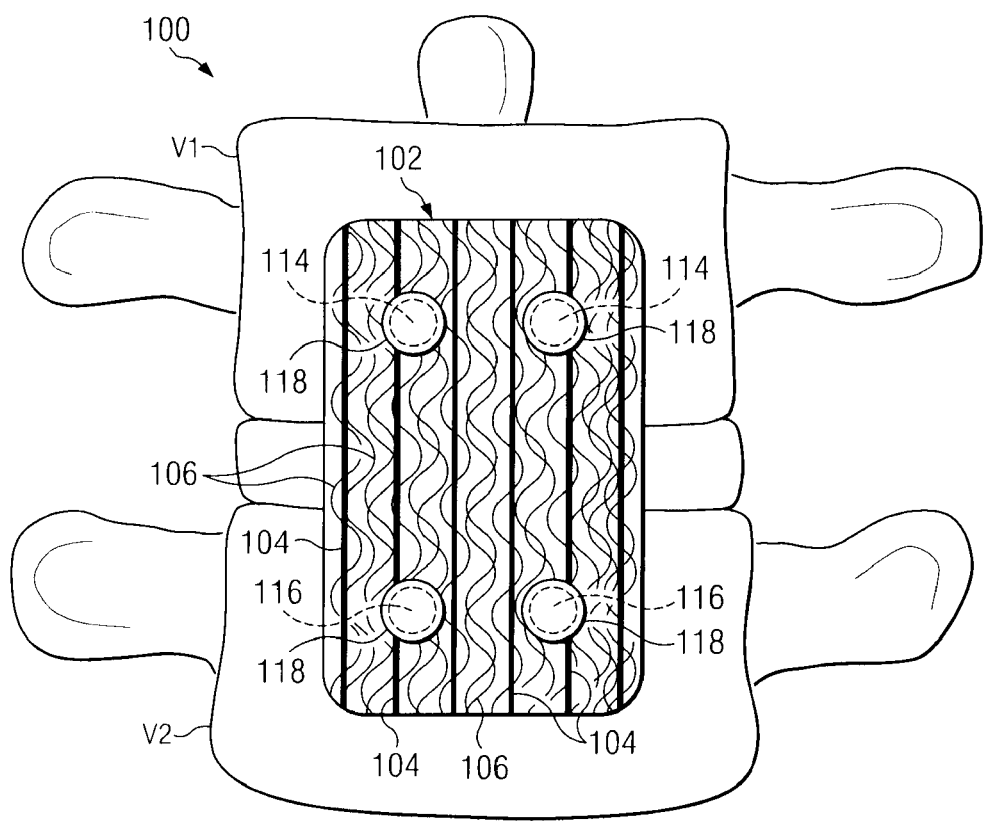
FIG. 2 is an anterior view of two vertebrae connected with a vertebral augmentation system according to one embodiment of the present disclosure.

The present disclosure relates generally to the field of orthopedic surgery, and more particularly to systems and methods for stabilizing a spinal joint. For the purposes of promoting an understanding of the principles of the invention, reference will now be made to embodiments or examples illustrated in the drawings, and specific language will be used to describe the same. It will nevertheless be understood that no limitation of the scope of the invention is thereby intended. Any alteration and further modifications in the described embodiments, and any further applications of the principles of the invention as described herein are contemplated as would normally occur to one skilled in the art to which the disclosure relates.

Referring first to FIG. 1, a side view of an exemplary spinal column is shown. The letters C, T and L refer to three sections of the spine respectively the cervical, thoracic and lumbar regions. The spinal regions are made up of vertebrae separated by intervertebral discs, including lumbar vertebrae V1, V2 separated by intervertebral disc I.

Referring next to the anterior view of FIG. 2, the reference numeral 100 refers to a lumbar spinal joint comprising vertebrae V1, V2, and intervertebral disc I. Although the illustration depicts a lumbar spinal joint, it is understood that the devices, systems, and methods of this disclosure may also be applied to all regions of the vertebral column, including the cervical and thoracic regions. A vertebral augmentation system 102 extends between vertebrae V1, V2 and across the disc I. It is understood that in some patients the disc I may have been fused or resected and replaced with a motion preserving device. The vertebral augmentation system may restore the functional support of a resected or damaged ligament by providing support against tension, torsion and shear forces on the joint 100.

As shown in FIGS. 2 and 3a, the vertebral augmentation system 102 comprises a biocompatible mesh which forms a plate or sheet like textile. The mesh is formed by a plurality of elastic strands 104 which are generally depicted by thick lines and inelastic strands 106 which are generally depicted as thin lines. Each of the elastic strands 104 has a length in an unloaded state and a maximum extension achieved during tensile loading, prior to rupture or other failure. Each of the inelastic strands 106 has a length in an unloaded state and a maximum extension achieved during tensile loading, prior to failure. The terms "elastic" and "inelastic" are understood to be relative terms, such that the materials used to create the inelastic strands may be semi-elastic, having an elasticity, albeit reduced, relative to the elasticity of the elastic strands. In addition, an individual strand may also be constructed of multiple materials, including elastic, semi-elastic, and inelastic, to obtain a desired response.

A wavy line indicates a slack strand and a straight line indicates a strand in tension that may or may not have begun to undergo elastic deformation. The elastic strands 104 may be woven, braided, or otherwise intertwined with the inelastic strands 106 to form the biocompatible mesh. It should be noted that although elastic strands in tension or under zero load are represented as straight lines, in practice, an elastic strand under tension may, in fact, be curved or bent where the strand is intertwined or otherwise in contact with another strand.

The mesh forms a rectangular block having a length or height H, a width W, and a thickness or depth D. In this embodiment, each of the dimensions H, W, and D have a different measurement, such that the mesh has a longer height H than width W or depth D, and width W is greater than depth D. It is understood that in an alternative embodiment, any of the dimensions H, W, or D may be as thin as a single strand 104 or 106. For example, minimizing the dimension D would result in a relatively thin, sheet-like fabric having little or no weaving across the dimension D. In still another embodiment, the mesh may form a thicker block. Suitable dimensions for a block style system may be, for example, 18 mm across the width dimension W and 30 mm along the length dimension L. Further, one dimension may vary across another dimension. For example the depth dimension D may vary across the height dimension H of the mesh.

As shown in FIG. 3a, in this embodiment the strands 104, 106 are woven to form a surface 108 of the mesh that lies generally orthogonal to a surface 110, both of which are generally orthogonally disposed to a surface 112. In this embodiment, the surfaces 108, 110, 112 are relatively flat or planar, however in alternative embodiments the surfaces may be curved. It is understood that a "surface" may refer to the outer boundary of an open weave of strands and need not necessarily indicate a solid face. Further, the surfaces may be curved or extend at non-orthogonal angles to each other.

A portion of the strands 104, 106 may extend along the height dimension H in a generally parallel array. Others of the strands 104, 106 may extend along the width W or depth D dimensions. Still others of the strands 104, 106 may extend at oblique angles across the mesh. As will be described in greater detail below, the configuration of the strands 104, 106 may impart desired directional elasticity and elastic limiters to the vertebral augmentation device.

As described above, the strands 104 may be formed from elastic material, and the strands 106 may be formed from inelastic, semi-elastic, or less elastic material than the elastic material of the strands 104. Exemplary elastic materials include polyurethane, silicone, silicone-polyurethane, polyolefin rubbers, hydrogels, and the like. Other suitable elastic materials may include NITINOL or other superelastic alloys. Further, combinations of superelastic alloys and non-metal elastic materials may be suitable to form elastic strands. The elastic materials may be resorbable, semi-resorbable, or non-resorbable.

Exemplary inelastic materials include any suitable biocompatible material including, for example, polymers, such as polyetheretherketone (PEEK), polyethylene terephthalate (PET), polyester, polyetherketoneketone (PEKK), polylactic acid materials (PLA and PLDLA), polyaryletherketone (PAEK), carbon-reinforced PEEK, polysulfone, polyetherimide, polyimide, ultra-high molecular weight polyethylene (UHMWPE), and/or cross-linked UHMWPE, among others. Metals or ceramics can also be used, such as cobalt-chromium alloys, titanium alloys, nickel titanium alloys, NITINOL, memory wire and/or stainless steel alloys, calcium phosphate, alumina, and/or pyrolytic carbon.

In an alternative embodiment, the mesh formed of the elastic and inelastic strands may be embedded in a matrix material such as an elastomeric material including any of the elastic materials listed above.

The strands can be manufactured to various scales depending on the desired properties. For instance, in one embodiment, the mesh is woven from strands with a cross-section in the nano-scale range. Other suitable strand cross-sections may be in the micro-scale or molecular scale range. Alternatively, a macro-scale may be used to weave the mesh, which results in a braided, knitted, or other-wise intertwined pattern. In a further variation, the resulting mesh is built-up or woven, for example, to produce, fabric, ribbons, tape, sleeves, loops, cables, braids, solid shapes, flat shapes, etc. In an additional variation, the density of the woven pattern is also varied to make the mesh more or less porous. For instance, one desired porosity may be in the range of 250 to 750 micrometers and another desired porosity may be approximately 500 micrometers.

Referring again to FIGS. 2 and 3a, the vertebral augmentation system 102 may include a set of upper connection features or anchor sites 114 and lower connection features 116 which in this embodiment are apertures extending through the mesh. The connection features 114, 116 may include grommets, rings, eyelets or other structure to maintain passage through the mesh. Bone fixation elements 118 may be inserted through the connection features 114 to fix the mesh of strands 104, 106 to the vertebral joint 100. The bone fixation elements 118, in this embodiment are bone screws, but in alternative embodiments bone fixation elements may be nails, anchors, adhesives, or other types of materials and structures able to hold the mesh to the bone. It is understood that the connection features need not be apertures, but may be tabs, adhesives, or other materials or structures able to hold the mesh to the bone without extending through the mesh.

In this embodiment, the vertebral augmentation system 102 may be installed through an anterior surgical approach in which the anterior surface of the vertebrae V1, V2 are exposed along with the intervertebral disc I. All or a portion of the anterior longitudinal ligament may be moved or removed. The vertebral augmentation system 100 may be placed such that an upper surface contacts vertebral body V1 and a lower surface contacts vertebral body V2. The bone fixation elements 118 may be drilled into the vertebral bodies V1, V2 through the connection features 114, 116 to hold the mesh to the joint. In an alternative embodiment, the bone fixation elements may be inserted first with the mesh later attached to the fixation elements. As installed, the surface of the vertebral augmentation system 102 may be in direct contact with the vertebrae V1, V2. The surgeon may arrange the vertebral augmentations system 100 and the bone fixation elements 118 to achieve a desired level of support from the system. Generally, the system 102 may be installed such that the elastic strands 104 are in slight tension or will become tensed upon slight movement of the spinal joint 100 such as extension or lateral bending motion. The tautness of the system 102 may determine the initial constraint placed upon the joint 100. The system 102 may be trimmed or otherwise modified to provide a better fit upon attachment to the vertebrae.

As installed, the system 102 may permit motion in the vertebral joint 100 while limiting excessive motion. For example, with an anteriorly placed system, extension of the joint 100 may cause the elastic strands 104 to stretch, permitting the patient's extension motion. To limit over extension and to prevent the rupture of the elastic strands 104, the inelastic strands 106 may act to prevent the elastic strands 104 from reaching maximum extension. FIG. 3b depicts the system 102 in an unloaded state. As can be seen, the inelastic strands 106 are slack or slightly bunched while the elastic strands 104 are elongated and not slack. It is understood that although the elastic strands 104 are represented as straight lines when having no slack, in practice, an elastic strand under tension and having no slack may, in fact, be curved or bent where the strand is intertwined or otherwise in contact with another strand. As shown in FIG. 3c, when the system 102 is placed in tensile loading through, for example, extension motion, lateral bending motion, or torsional motion, the elastic strands 104 become stretched to accommodate the movement while the slack in the inelastic strands 106 is let out to accommodate the stretching of the elastic strands. The stretching of the elastic strands 104 will be stopped when the inelastic strands 106 reach maximum extension, thus placing a stop limit on the elastic strands. In this embodiment, the inelastic strands 106 do not place a resistance on extension of the elastic strands 104 until the slack is consumed. Because of the combination of the elastic and inelastic strands 104, 106, the total system 102 may exhibit non-linear elastic behavior.

For completely inelastic strands, the stop limit may occur when the inelastic strands are uncoiled to their full length. Where the inelastic strands have elastic properties, the stop limit for the elastic strands will be reached when the inelastic strands reach not only the unfurled length, but also the maximum extension including any stretching permitted by the material's elastic properties.

Although an open anterior surgical approach is described, it is understood that the system 102 may be installed using minimally invasive techniques. Further, the system 102 or other systems to be described may be implanted using lateral or posterior surgical approaches.

Figure 4:
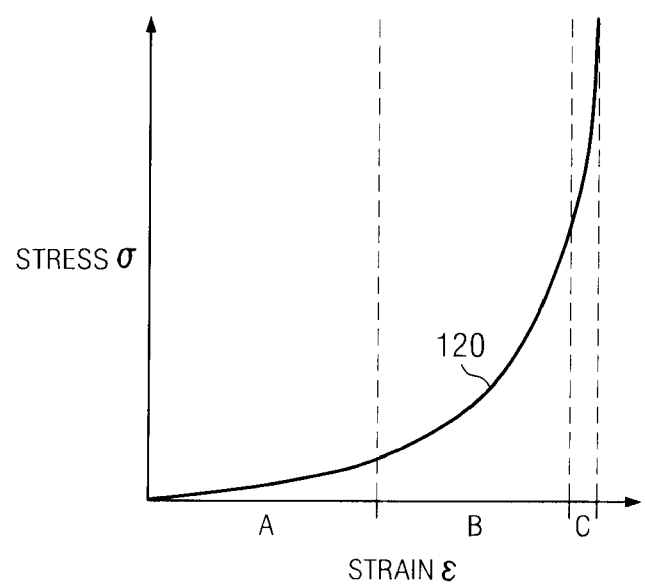
FIG. 4 is a stress-strain curve showing an approximate elasticity of a vertebral augmentation system according to an embodiment of this disclosure.

Referring now to FIG. 4, a stress-strain curve 120 for a vertebral augmentation system is shown which approximates the behavior of natural tissue such as a natural ligament. Strain, or elongation $\epsilon$, is indicated on the horizontal axis and stress $\sigma$ is indicated on the vertical axis. The non-linear curve 120 is shown and may represent a desired stress-strain curve for any of the embodiments of this disclosure. The curve 120 is approximately linear over section A, indicating that additional loading of the mesh will result in a proportional stretching of the mesh. When curve 120 reaches section B, the increase in elongation $\epsilon$ slows proportional to the increase in stress $\sigma$ to the mesh. Over section B, the curve is non-linear which may correspond to the behavior of the inelastic strands limiting elastic deformation of the elastic strands. When curve 120 reaches section C, an increase in stress could result in failure of the elastic strands by exceeding the elastic limit; however, the inelastic strands prevent further elongation of the elastic strands thereby preventing the elastic strands from reaching the elastic limit. Therefore, section C of curve 120 represents a limit to elongation even with increasing amounts of stress. The combination of the sections A, B, and C of the curve 120 represent the non-linear behavior of an exemplary mesh that may be suitable to replace or augment natural tissue.

Figure 5:
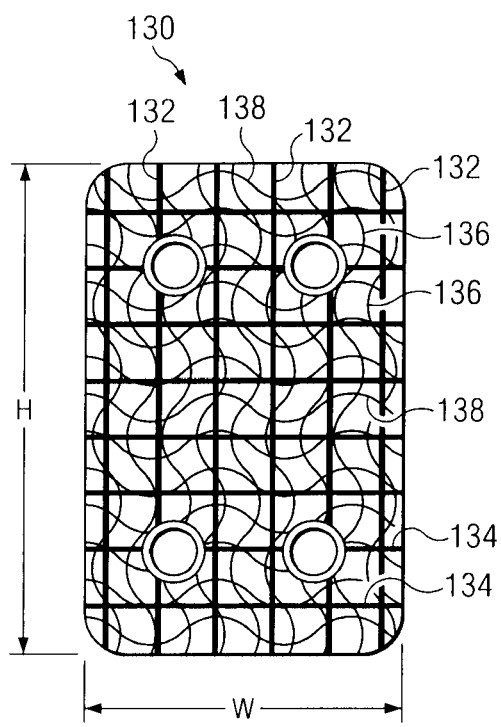
FIGS. 5-8 are vertebral augmentation systems according to different embodiments of the present disclosure.

Referring now to FIG. 5, a vertebral augmentation system 130 may be substantially similar to the system 120 with the differences to be described. In this embodiment, the system 130 comprises a mesh formed of elastic strands 132 and 134 and inelastic strands 136 and 138. This mesh may be pre-loaded to remove slack from the elastic strands 132, 134. The inelastic strands 136 and 138 are in a slack state shown by wavy lines. Strands 132 and 136 are substantially parallel to each other and extend along the height dimension H of the system 130. Thus, strands 132 and 136 may be suitable to permit extension of the affected joint while resisting over extension. Strands 134 and 138 are oriented substantially transverse to strands 132 and 136, extending across the width dimension W of the system 130. Thus, strands 134 and 138 may function to permit limited motion of the affected joint under torsional or shear loading.

Figure 6:
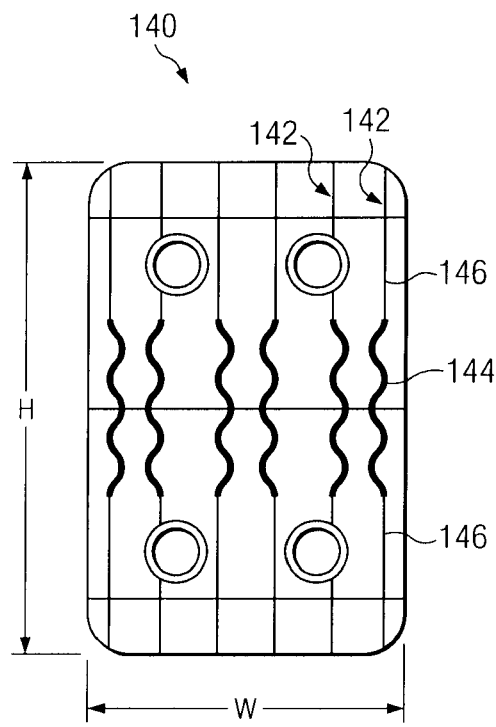

Referring now to FIG. 6, a vertebral augmentation system 140 may be substantially similar to the system 120 with the differences to be described. In this embodiment, the system 140 comprises a mesh formed of strands 142 having both elastic portions 144 and inelastic portions 146. In this embodiment, the inelastic portions 146 may be tensioned with the elastic portions 144 remaining slack. Constructing strands of varying elasticity may provide further allow the system 140 to function in a way that closely resembles a natural tissue.

Figure 7:
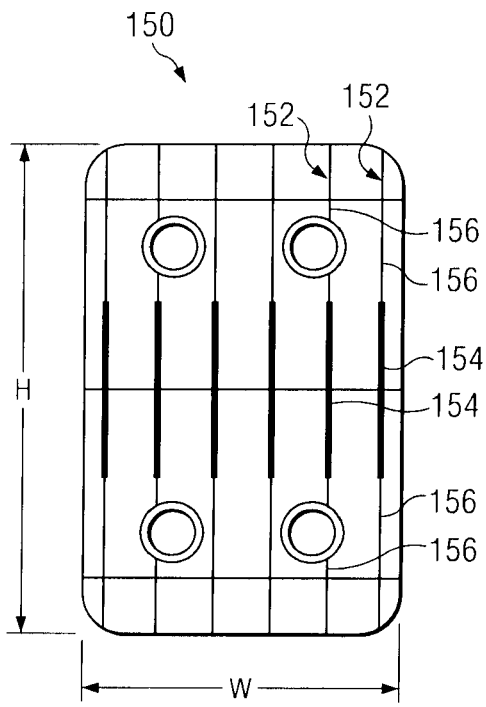

Referring now to FIG. 7, a vertebral augmentation system 150 may be substantially similar to the system 120 with the differences to be described. In this embodiment, the system 150 comprises a mesh formed of strands 152 having both elastic portions 154 and inelastic portions 156. In this embodiment, the inelastic portions 156 and the elastic portions 154 may be tensioned, with the elastic portions allowing for further stretching of the system 120.

Figure 8:
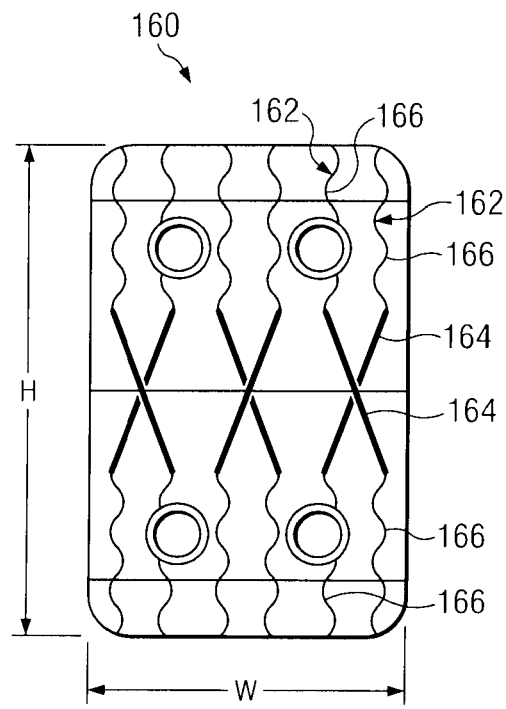

Referring now to FIG. 8, a vertebral augmentation system 160 may be substantially similar to the system 120 with the differences to be described. In this embodiment, the system 160 comprises a mesh formed of strands 162 having both elastic portions 164 and inelastic portions 166. In this embodiment, the inelastic portions 166 may be slack with the elastic portions 164 in tension. In this embodiment, the elastic portions 164 may cross over one another to enable the resultant mesh to behave in a desired manner.

Figure 9A:
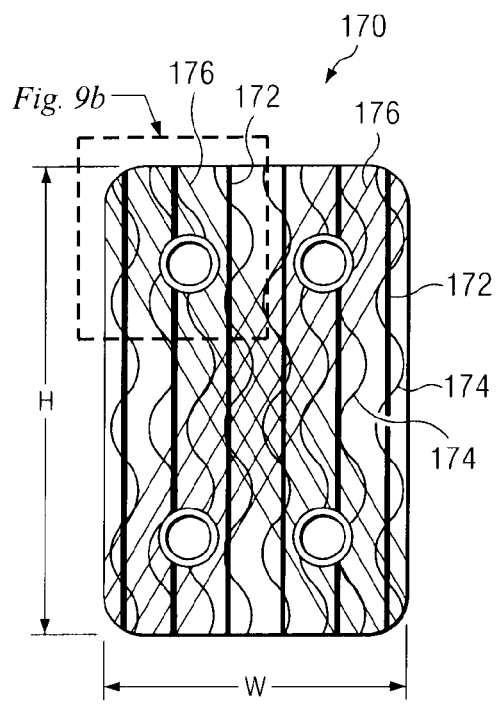
FIG. 9a is a vertebral augmentation system according another embodiment of the present disclosure.
Figure 9B:
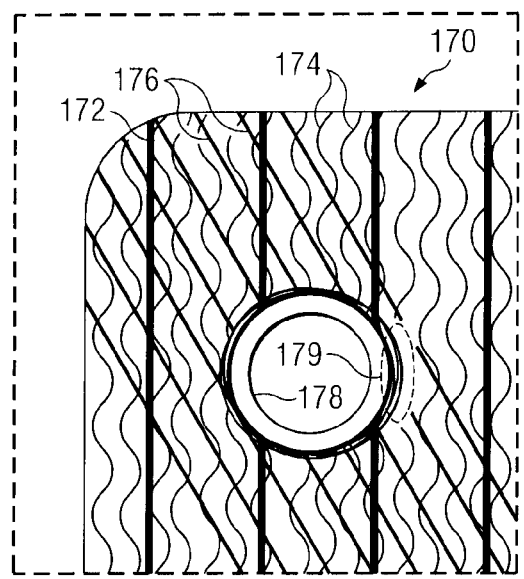
FIG. 9b is a detailed view of the vertebral augmentation system according to the embodiment of FIG. 9a showing strands wrapped around a connection component.

Referring now to FIGS. 9a and 9b, a vertebral augmentation system 170 may be substantially similar to the system 120 with the differences to be described. In this embodiment, the system 170 comprises a mesh formed of elastic strands 172 that are in tension, inelastic strands 174 that are slack, and inelastic strands 176 that extend diagonally across the length L and width W of the system 170. The diagonal inelastic strands 176 may function to resist and support torsional or shear loading on the affected joint. As shown in FIG. 9b, the strands 172, 174, 176 may wrap or form loops 179 around a connection feature 178. The loops 179 may enable the strands 172, 174, 176 to maintain their strength as they pass around the connection feature 178.

Figure 10:
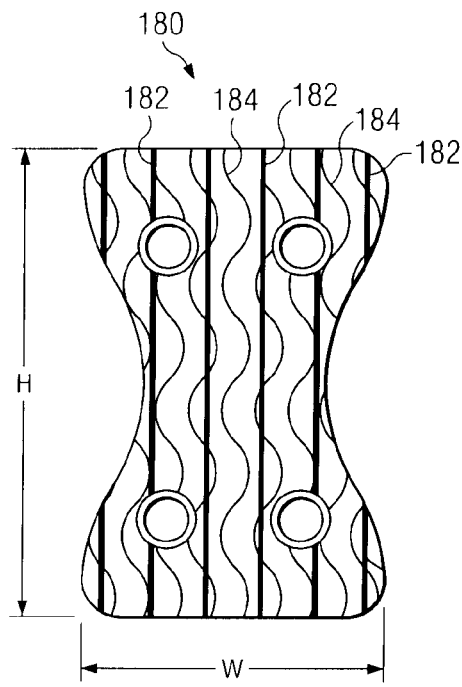
FIG. 10 is a vertebral augmentation system having an hour glass shaped profile.

Referring now to FIG. 10, a vertebral augmentation system 180 may be substantially similar to the system 120 with the differences to be described. In this embodiment, the system 180 includes a mesh formed of elastic strands 182 and inelastic strands 184. The system 180 may have an hour-glass profile or shape such that the boundary of the mesh includes both concave and convex curves along the height dimension H.

Figure 11:
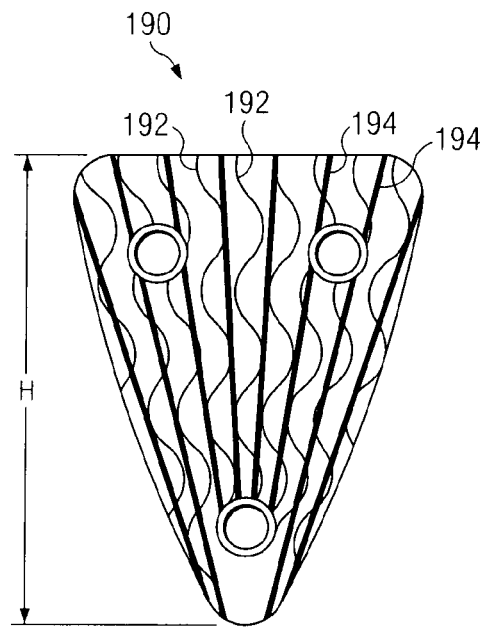
FIG. 11 is a vertebral augmentation system having a triangular shaped profile.

Referring now to FIG. 11, a vertebral augmentation system 190 may be substantially similar to the system 120 with the differences to be described. In this embodiment, the system 190 includes a mesh formed of elastic strands 192 and inelastic strands 194. The system 190 may have a triangular shape such that the boundary of the mesh is tapered along the height dimension H.

In still other alternatives, the mesh may have other suitable shapes such as rod shaped. A rod shaped embodiment is described in pending U.S. patent application Ser. No. 11/413,448, which is incorporated by reference herein. Other suitable shapes may include a sleeve shaped mesh, a corrugated plate mesh, or an X-shaped mesh.

Figure 12:
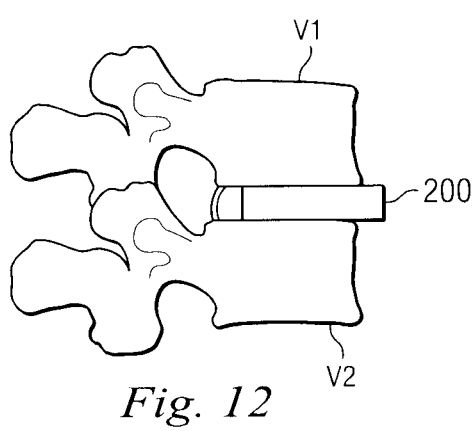
FIG. 12 is a sagittal view of a vertebral joint including a vertebral augmentation system inserted between vertebral bodies.

Referring now to FIG. 12, the intervertebral disc I may be replaced with a vertebral augmentation system 200 which in this embodiment is an intervertebral device.

Figure 13:
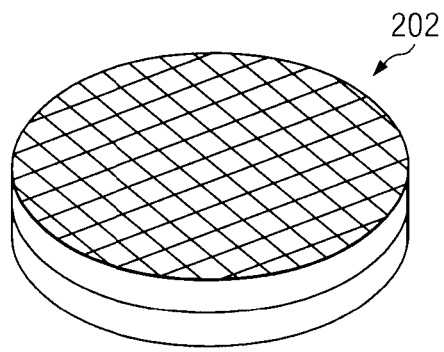
FIG. 13 is a perspective view of a vertebral augmentation system that may be inserted in a disc space.
Figure 14A:
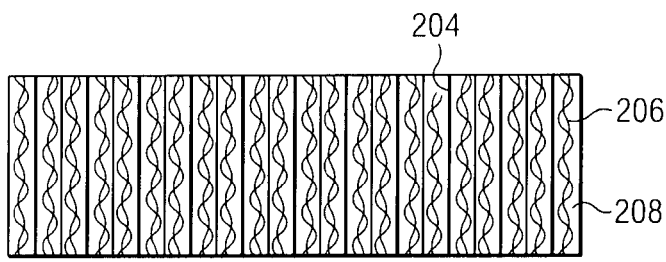
FIG. 14a is a cross sectional view of the vertebral augmentation system of claim of FIG. 13 showing a mesh system embedded in a matrix material.
Figure 16:
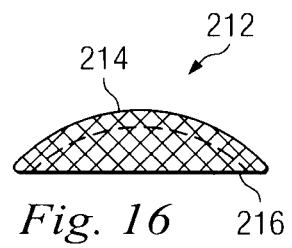
FIG. 16 is a side view of a dome shaped vertebral augmentation system that may be inserted in a disc space.

Referring now to FIGS. 13 and 14a, in one embodiment, the system 200 is a mesh structure 202 constructed substantially similar to the system 102. The structure 202 comprises elastic strands 204 intertwined with inelastic strands 206 to form a puck-like structure that may be inserted into the space between vertebrae V1 and V2. In this embodiment, the mesh formed of strands 204, 206 may be embedded in a matrix material 208. Suitable matrix materials may include elastic materials such as those listed above. The resulting structure may be relatively non-porous with generally solid surfaces. This matrix embedded embodiment may have a relatively high compressive strength and be particularly suited to maintain the height of the disc space. As shown in FIG. 16, a vertebral augmentation system 212, which may be substantially similar to system 200, has a dome shaped upper surface 214 and a relatively flat bottom surface 216. The system 212 may also be suitable for replacing or augmenting a portion of the disc I.

Figure 14B:
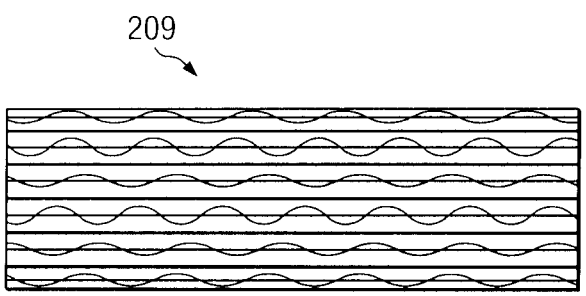
FIG. 14b is a cross sectional view of an alternative vertebral augmentation system.

Referring now to FIG. 14b, in this embodiment, an intervertebral mesh structure 209 may be substantially similar to the system 200 however in this embodiment, the elastic and inelastic strands are configured to extend in a direction transverse to the strands in system 200. When installed in an intervertebral disc space between vertebrae V1, V2 and subjected to compressive loading, the elastic strands may stretch laterally and the inelastic strands may uncoil in a lateral direction, allowing the structure 209 may expand laterally in response to the compressive load until the inelastic strands act as a limit to further expansion.

Figure 15:
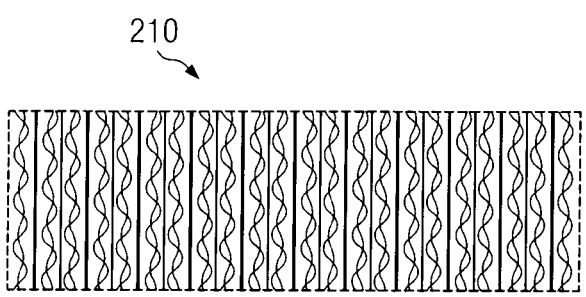
FIG. 15 is a cross sectional view of an alternative vertebral augmentation system which omits the matrix material.

Referring now to FIG. 15, in an alternative embodiment, an intervertebral mesh structure 210 may be a generally open and porous weave with no matrix material binding the strands in the structure. The porous nature of the mesh structure 210 may allow for ingrowth of natural collagen and bone, ultimately permitting fusion of the joint. It is further contemplated to combine the properties of systems 202 and 210 to have a mesh block with a durable, encapsulated core that remains porous on the outside surfaces.

In an alternative embodiment, a vertebral augmentation device may include inelastic strands extending transversely to the elastic strands or at an oblique angle to the elastic strands. For example, a set of elastic strands may be grouped toward the center of the augmentation device and a fabric of inelastic or elastic/inelastic strands may be wrapped around the elastic strands with the inelastic strands of the fabric at an oblique angle to the elastic strands to limit the extension of the elastic strands under tensile loading.

Although only anterior and intervertebral embodiments have been described in detail, the mesh formations may be used in the posterior area of the vertebral column such as in the interspinous process space.

The foregoing embodiments of the mesh system may be provided individually or in a kit providing a variety of sizes of components as well as a variety of strengths. It is also contemplated that the mesh's characteristics may be color coded or otherwise indicated on the mesh itself to expedite identification of a desired mesh.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," "right," "cephalad," "caudal," "upper," and "lower," are for illustrative purposes only and can be varied within the scope of the disclosure. Further, the embodiments of the present disclosure may be adapted to work singly or in combination over multiple spinal levels and vertebral motion segments. Also, though the embodiments have been described with respect to the spine and, more particularly, to vertebral motion segments, the present disclosure has similar application to other motion segments and parts of the body. In the claims, means-plus-function clauses are intended to cover the elements described herein as performing the recited function and not only structural equivalents, but also equivalent elements.

I claim:

1. A vertebral augmentation system comprising:
    a biocompatible mesh sheet having a first end and a second end and including:
        a plurality of first strands, the first strands being elastic strands of an elastic material and having a first end and a second end, the first strands having a first length measured between the first and second ends when in an unstretched condition and having a second length measured between the first and second ends when the elastic material is stretched to a stretched condition,
        a plurality of second strands, the second strands being inelastic strands of an inelastic material and having a first end and a second end, the second strands having a first length measured between the first and second ends when the second strands are slack, the second strands being more bent when the inelastic second strands are slack, the second strands having a second length measured between the first and second ends when the second strands are taut, the inelastic second strands being relatively less bent when the strands are taut, a first interface portion adapted to contact a first vertebral bone, and a second interface portion adapted to contact a second vertebral bone, wherein in response to loading applied when the first vertebral bone moves relative to the second vertebral bone, the distance between the first and second ends of the plurality of elastic first strands increases as a result of elastic stretching and the distance between the first and second ends of the plurality of inelastic second strands increases as a result of straightening as the slack decreases and as the second strands become more taut such that the second strands create a stop-limit on the amount of movement of the mesh sheet and on the amount of stretch of the plurality of elastic first strands in a manner that provides the mesh sheet with a non-linear elastic behavior when the first vertebral bone moves relative to the second vertebral bone.

2. The vertebral augmentation system of claim 1 wherein the biocompatible mesh sheet further includes a length, a width, and a depth, each having a different measurement.

3. The vertebral augmentation system of claim 1 wherein the biocompatible mesh sheet further includes a first generally flat surface disposed generally orthogonally relative to a second generally flat surface.

4. The vertebral augmentation system of claim 3 wherein the biocompatible mesh sheet further includes a third generally flat surface disposed generally orthogonally relative to the first and second generally flat surfaces.

5. The vertebral augmentation system of claim 1 wherein the first interface portion is adapted to contact an anterior face of a first vertebral body.

6. The vertebral augmentation system of claim 1 wherein the first interface portion is adapted to contact an endplate of a first vertebral body.

7. The vertebral augmentation system of claim 1 wherein, in an unloaded state, the plurality of second strands is slack.

8. The vertebral augmentation system of claim 1 further comprising a matrix component wherein the biocompatible mesh sheet is at least partially embedded in the matrix component.

9. The vertebral augmentation system of claim 8 wherein the matrix component is an elastic.

10. The vertebral augmentation system of claim 1 further comprising a first connection feature for affixing the first interface portion to the first vertebral bone and a second connection feature for affixing the second interface portion to the second vertebral bone.

11. The vertebral augmentation system of claim 10 wherein the first and second connection features are apertures adapted to receive fixation members.

12. The vertebral augmentation system of claim 11 wherein at least some of the plurality of first or second strands wrap around the apertures.

13. The vertebral augmentation system of claim 1 wherein the biocompatible mesh sheet exhibits the non-linear elastic behavior when subjected to a tensile loading.

14. The vertebral augmentation system of claim 1 wherein when at least some of the plurality of inelastic second strands become taut, further extension of at least some of the plurality of first strands is stopped.

15. The vertebral augmentation system of claim 1 wherein the plurality of first strands have a first unloaded longitudinal length and the plurality of second strands have a second unloaded longitudinal length greater than the first unloaded length.

16. The vertebral augmentation system of claim 1 wherein the biocompatible mesh sheet has a rectangular profile.

17. The vertebral augmentation system of claim 1 wherein the plurality of first strands extends between the first and second ends and the plurality of second strands extends between the first and second ends.

18. The vertebral augmentation system of claim 1 wherein a first axis extends between the first end and the second end and at least some of the plurality of first or second strands extend transverse to the first axis.

19. The vertebral augmentation system of claim 1 wherein the at least one elastic material is a polymer.

20. The vertebral augmentation system of claim 1 wherein the at least one inelastic material is a metal or ceramic.

21. The vertebral augmentation system of claim 1 wherein the plurality of first and second strands are intertwined in at least two dimensions.

22. An artificial anterior spinal ligament system comprising:

a multi-dimensional, bio-compatible mesh of elastic and inelastic strands having a periphery; the mesh having a first end adapted to engage an anterior face of a first vertebral bone and a second end adapted to engage an anterior face of a second vertebral bone, wherein the elastic strands extend between the first end and the second end, and are adapted to traverse a space between the first and second vertebral bones, the elastic strands having a first elasticity and a first longitudinal length and a first linear length, the first longitudinal length measured along the longitudinal length of the elastic strands between the first and second ends when in an unstretched condition, the first linear length being measured as a straight line distance between the first end and the second end, wherein the inelastic strands extend between the first end and the second end, and are adapted to traverse the space between the first and second vertebral bones, the inelastic strands having less elasticity than the elastic strands and a second longitudinal length greater than the first longitudinal length and having a second linear length, the second longitudinal length being measured along the longitudinal length of the inelastic strands and the second linear length being measured as a straight line distance between the first end and the second end, the inelastic strands being arranged to extend between the first and second ends in a slack condition when the mesh is in an unloaded condition, and wherein when the first and second ends of the mesh move apart, the second longitudinal length of the inelastic strands is relatively unchanged while the second linear length of the inelastic strands increases, and wherein when the first and second ends of the mesh move apart, the first longitudinal length of the elastic strands increases at substantially the same rate as the first linear length, the first longitudinal length of the elastic strands increasing until the slack in the inelastic strands decreases such that the inelastic strands limit the stretch of the elastic strands and prevent over-extension of the elastic strands.

23. The system of claim 22 wherein the inelastic strands are slack when in a relaxed state and the slack is consumed during extension of the elastic strands and wherein the inelastic strands prevent further extension of the elastic strands when the slack is fully consumed.

24. The system of claim 22 configured to operate according to a non- linear stress-strain elasticity curve.

25. The system of claim 22 further comprising anchor sites, an anchor site disposed at each of the first and second ends, each anchor site configured to receive a fixation element for operably securing the mesh to the vertebral bones.

26. The system of claim 22 wherein the mesh periphery is substantially patterned into a rectangular shape.

* * * * *